United States Patent [19]

Sasaki

[11] Patent Number: 4,478,085
[45] Date of Patent: Oct. 23, 1984

[54] ULTRASOUND DIAGNOSIS APPARATUS
[75] Inventor: Hiroshi Sasaki, Ootawara, Japan
[73] Assignee: Tokyo Shibaura Denki Kabushiki Kaisha, Japan
[21] Appl. No.: 408,276
[22] Filed: Aug. 16, 1982
[30] Foreign Application Priority Data
  Aug. 18, 1981 [JP] Japan ................. 56-129529
[51] Int. Cl.³ .......................... G01N 29/00
[52] U.S. Cl. ....................... 73/625; 73/626; 73/642; 73/628; 128/660; 367/155
[58] Field of Search ............ 73/625, 628, 642, 626; 367/43, 45, 105, 155; 128/660

[56] References Cited
U.S. PATENT DOCUMENTS

| | | | |
|---|---|---|---|
| 3,277,451 | 10/1966 | Parssinen . | |
| 3,281,776 | 10/1966 | Ruehle | 367/45 |
| 3,457,543 | 7/1969 | Akervold et al. . | |
| 3,701,154 | 10/1972 | McKinney . | |
| 3,815,409 | 6/1974 | Macovski | 73/642 |
| 3,833,825 | 9/1974 | Haan . | |
| 3,936,791 | 2/1976 | Kossoff . | |
| 4,016,750 | 4/1977 | Green | 73/629 |
| 4,016,751 | 4/1977 | Kossoff | 73/642 |
| 4,138,895 | 2/1979 | Mezrich | 73/642 |
| 4,145,931 | 3/1979 | Tancrell . | |
| 4,168,628 | 9/1979 | Vilkomerson . | |
| 4,228,804 | 10/1980 | Holasek et al. . | |
| 4,241,610 | 12/1980 | Anderson . | |
| 4,305,296 | 12/1981 | Green et al. . | |
| 4,307,613 | 12/1981 | Fox | 73/626 |
| 4,312,050 | 1/1982 | Lucas | 367/43 |
| 4,372,323 | 2/1983 | Takemura et al. . | |
| 4,392,379 | 4/1983 | Yamaguchi . | |
| 4,403,314 | 9/1983 | Tournois . | |

FOREIGN PATENT DOCUMENTS 8001537 8/1980 European Pat. Off. .
56-57391 5/1981 Japan .

Primary Examiner—Howard A. Birmiel
Attorney, Agent, or Firm—Cushman, Darby & Cushman

[57] ABSTRACT

An ultrasound diagnosis apparatus comprising, a pulser, a transducer connected to the pulser, which is driven by drive pulses from the pulser to radiate ultrasound wave toward an object and to receive echoes returned from the object to convert the echoes into electrical signals, the thickness of the transducer changing in a direction orthogonal to the ultrasound beam traveling direction, a filter connected to the transducer for filtering the electrical echo signals from the transducer with the filter characteristic which is changed according to a change of the thickness of the transducer, signal processing circuit connected to the filter for processing the electrical echo signals passed through the filter to convert it into tomogram signal, and a monitor connected to the signal processing circuit for displaying a tomogram according to a tomogram signal from the signal processing circuit.

5 Claims, 12 Drawing Figures

ULTRASOUND DIAGNOSIS APPARATUS

BACKGROUND OF THE INVENTION

The present invention relates to an ultrasound diagnosis apparatus which can effectively change a width of a transducer array.

In ultrasound diagnosis apparatus, drive pulses generated by a pulse generator are applied to a transducer array. Then, the transducer array is excited by the drive pulses to radiate ultrasound pulses into an object under diagnosis. The echo pulses returned from the object are received by the transducer. The echo acoustic pulses are converted into corresponding electrical signals. The converted electrical signals are properly processed to be visible on a monitor in the form of a tomogram of the object. In ultrasound diagnosis apparatus, the diameter of the ultrasound beam radiated from the transducer array at the portion of the object being studied influences the resolution of the tomogram in the azimuth direction, i.e. a direction orthogonal to a propagating direction of the ultrasound beam, in such a way that the resolution of the tomogram increases as the convergence of the ultrasound beam at the portion under study increases. The diameter of the ultrasound beam is substantially equal to the width of the excited portion in the vicinity of the transducer array. When the transducer is made up of a number of transducer elements, the excited transducer elements may be referred to as the drive portion. In the one piece type transducer, the drive portion corresponds to the entire transducer portion. The resolution of the tomogram in the vincinity of the transducer array can be improved by reducing the width of the drive portion of the transducer array. With transducer arrays, the resolution of the tomogram can be improved by reducing the number of transducer elements. Away from the transducer array, the ultrasound wave expands due to diffusion, so that the diameter of its beam expands as it progresses. The expansion of the beam diameter is inversely proportional to the drive portion of the transducer array. Therefore, if the width of the drive portion is made small for improving the resolution at a location near the transducer, the expansion of the ultrasound beam diameter is large and the resolution at a short range is deteriorated. Thus, for improving the resolution, an apparent contradiction exists in that for improving the resolution in a short range, the width of the drive portion must be small, but for improving the resolution in a long range, it must be large. Further, the expansion of the ultrasound wave is inversely proportional to its frequency. Accordingly, the resolution in the azimuth direction also depends largely on the frequency of the ultrasound. This will be described in detail referring to FIG. 1 illustrating an expanding (ultrasound field) ultrasound beam radiated from a transducer array 1. The transducer array 1 is comprised of a plurality of transducer elements aligned in a series and with the same thickness, as viewed in the azimuth direction. A plan view of these arrayed transducer elements is indicated by reference numeral 1'. As seen from the figure, the diameter of the beam in the vicinity of the transducer array 1 is substantially equal to the width of the transducer array 1, irrespective of the frequency of the ultrasound wave. In a distant region from the transducer array, the beam changes its diameter with the frequency. In the figure, frequencies f1 to f3 of the ultrasound beams increase with their suffix numbers, $f1 < f2 < f3$. As seen from the figure, the larger the expansion of the beam, the lower the frequency of the ultrasound beam. Therefore, to make the expansion of the beam diameter small, it is necessary to select the frequency of the beam to be high. In this case, however, another problem arises in that the attenuation of the ultrasound wave in a living body increases with frequency. This implies that the high frequency components of the ultrasound beam become more attenuated as the beam goes deeper into the living body. Accordingly, when imaging deep in the living body, the low frequency components have great contribution to the resolution. In this respect, the frequency of the ultrasound beam must be limited below a given frequency. The consequence is a compromise between a proper beam diameter and a proper beam frequency. More explicitly, at an imaging plane $X_{l1}$ distanced "l1" from the transducer 1, the frequency component f3 is attenuated to almost zero. Accordingly, the resolution at this portion is determined by the frequency component at f2 with the beam diameter D2. Accordingly, the resolution at this measuring location depends on a compromise between the frequency f2 and the beam diameter D2. Further, at an imaging plane $X_{l2}$ distanced "l2" from the transducer array 1, the frequency components f2 and f3 are both lost and only the frequency component f1 is effective. The resolution at the imaging plane $X_{l2}$ is determined by the frequency component f1 and its diameter D3.

For the above background reason, the improvement of the resolution of a tomogram has a limit in both short and long ranges. Particularly, in the long range or in a deep measuring portion of the living body, a high resolution can not be obtained and a picture quality of a tomogram is poor.

SUMMARY OF THE INVENTION

Accordingly, an object of the present invention is to provide an ultrasound diagnosis apparatus with an improved resolution in the azimuth direction.

According to the present invention, there is provided an ultrasound diagnosis apparatus comprising: drive pulse generating means; transducer means connected to the drive pulse generating means, which is driven by drive pulses from the drive pulse generating means to radiate ultrasound wave toward an object and to receive echoes returned from the object to convert the echoes into electrical signals, the thickness of the transducing means changing in a direction orthogonal to the ultrasound beam traveling direction; filter means connected to the transducer means for filtering the electrical echo signals from the transducer means with the filter characteristic which is changed according to a change of the thickness of the transducer means; signal processing means connected to the filter means for processing the electrical echo signals passed through the filter means to convert it into a tomogram signal; and display means connected to the signal processing means for displaying a tomogram according to a tomogram signal from the signal processing means.

DETAILED DESCRIPTION OF THE PREFERRED EMBODIMENTS

Figure 1:
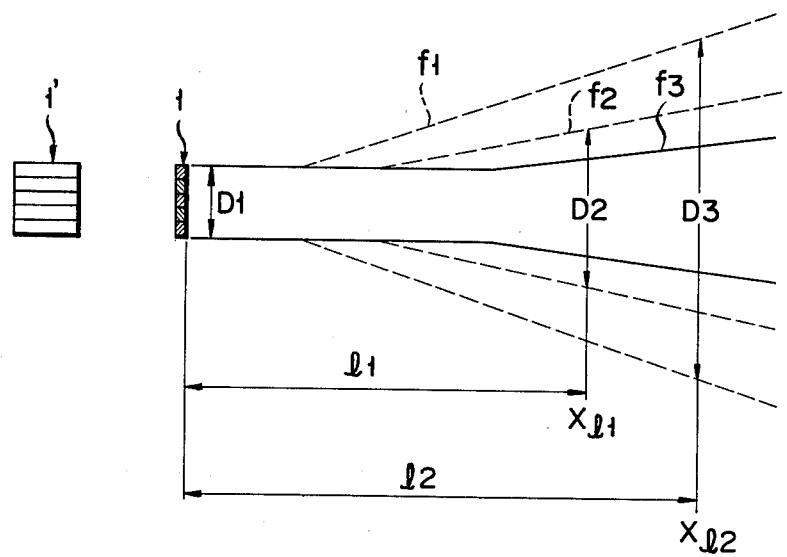
FIG. 1 shows an explanatory diagram of an ultrasound field formed by a prior transducer array.
Figure 2:
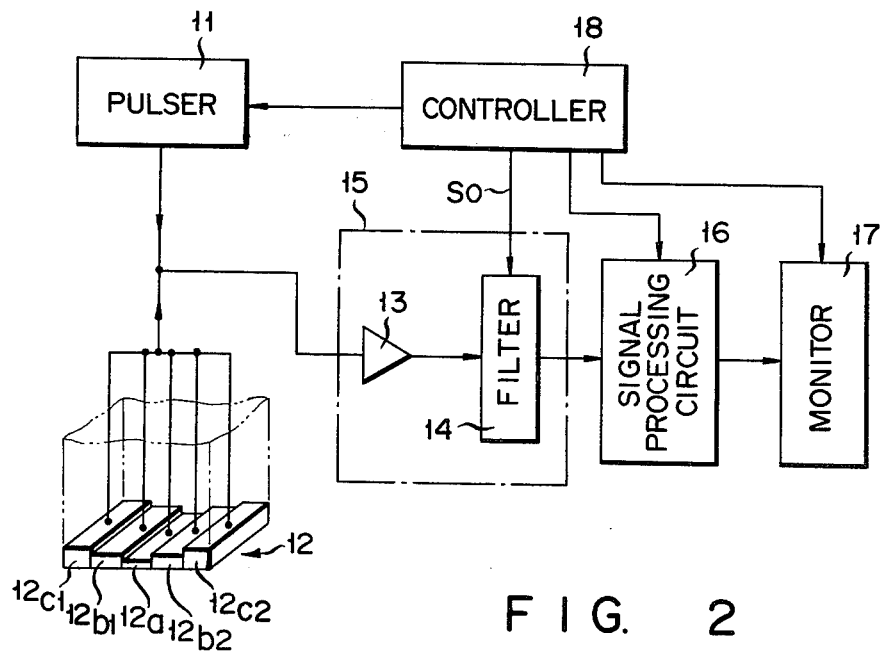
FIG. 2 is a block diagram of an embodiment of an ultrasound diagnosis apparatus according to the present invention.

Referring to FIG. 2, a pulser 11 produces a drive pulse at a fixed frequency rate, and is connected at the output terminal to a transducer 12 and to the input terminal of an amplifier 13. The output terminal of the amplifier 13 is connected to the input terminal of a band pass filter 14. The amplifier 13 and the filter 14 make up a receiver 15. The output terminal of the band pass filter 14 is connected to the input terminal of a signal processing circuit 16. The processing circuit 16 is connected to the input terminal of a monitor i.e. a display device 17. A controller 18 controls the operations of the pulser 11, the band pass filter 14, the signal processing circuit 16 and the monitor 17.

Figure 5:
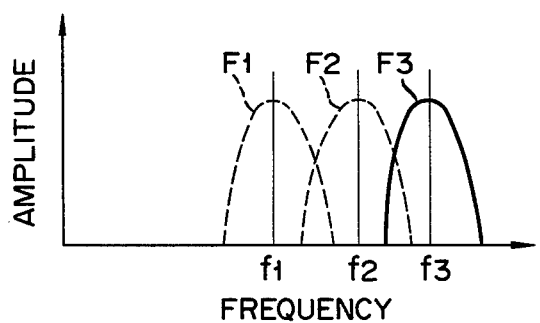
FIG. 5 shows a graph illustrating a filter characteristic of a filter used in the diagnosis apparatus.

As shown, the transducer 12 has a plurality of transducer elements 12a, 12b1, 12b2, 12c1 and 12c2, and these elements are arrayed such that their thickness decreases as the center of the transducer is approached, and the element 12a located at the center of the transducer array 12 is the thinnest. The transducer array 12 may be either of the separate type as illustrated or of the one-piece type. The filter 14 is of the dynamic type in which its center frequency shifts under control of the controller 18, with the same frequency band. As shown in FIG. 5, the center frequency shifts from f1 to f3 with its associated band pass characteristic curves F1 to F3.

Figure 6:
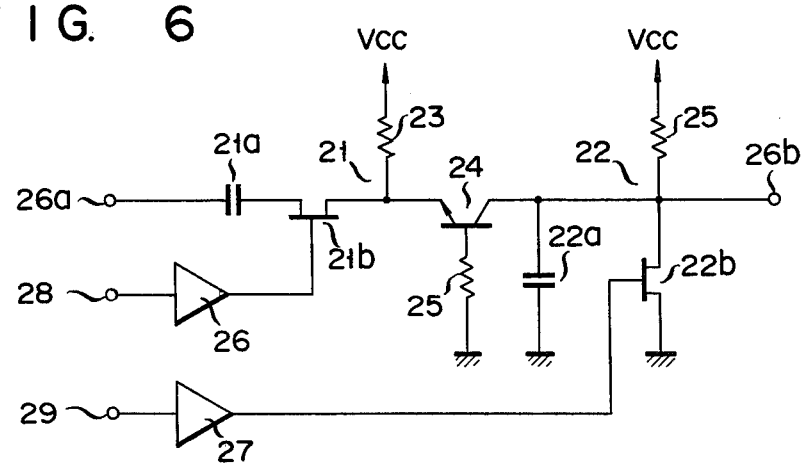
FIG. 6 shows a circuit diagram of a filter used in the present invention.
Figure 7:
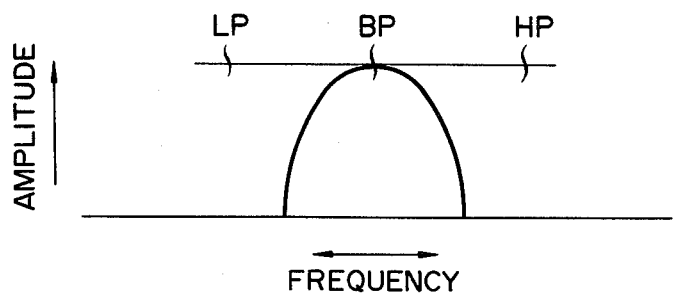
FIG. 7 shows a filter characteristic of the FIG. 6 filter.

The band pass filter 14 is comprised of a high pass filter 21 and a low pass filter 22, as shown in, for example, FIG. 6. 26a and 26b are input and output terminals of the filter 14, respectively. The high pass filter 21 is comprised of serially connected capacitor 21a and impedance element, e.g., FET 21b. The output terminal of FET 21b is connected to a power source $V_{CC}$ through a resistor 23 and also to the emitter of a transistor 24, the base of which is grounded through a resistor 25. The collector of the transistor 24 is grounded passing in parallel through a capacitor 22a and FET 22b of the low pass filter 22, and is also connected to an output terminal 26b. The collector of the transistor 24 is connected to a power source $V_{CC}$ through a resistor 25. Control signal input terminals 28 and 29 are connected to the gates of FETs 21b and 22b through amplifiers 26 and 27, respectively. When predetermined variable signals, for example, saw tooth signals are supplied from the controller 18 to the control signal input terminals 28 and 29, the impedances of the FETs 21b and 22b vary, so that the filtering characteristics of the high pass filter 21 and low pass filter 22 vary. As a result, as shown in FIG. 7, a band pass region BP, i.e. an overlap region of a high pass region HP and a low pass region LP, is shifted. Thus, a signal corresponding to the band pass region BP is obtained from the output terminal 26b.

The operation of the ultrasound diagnosis device as shown in FIG. 2 will be described.

The pulser 11 produces drive pulses at a fixed frequency under control of the controller 18. The drive pulse from the pulser 11 is applied to the transducer elements 12a, 12b1, 12b2, 12c1 and 12c2. Upon receipt of the drive pulse, these elements produce ultrasound waves at proper frequencies. The ultrasound waves radiated propagate through a living body and return from many portions in the living body with different acoustic impedance in the form of echoes. The echoes are received by the transducer array 12 where these are converted into corresponding electrical signals. The converted signals are inputted into the amplifier 13 and then is applied to the band pass filter 14. The band pass filter 14 filters the signals from the amplifier to pass only the signal components at a frequency within a given frequency band. The filtered out signals are properly processed and then applied to the monitor 17 where these are visualized.

Figure 3:
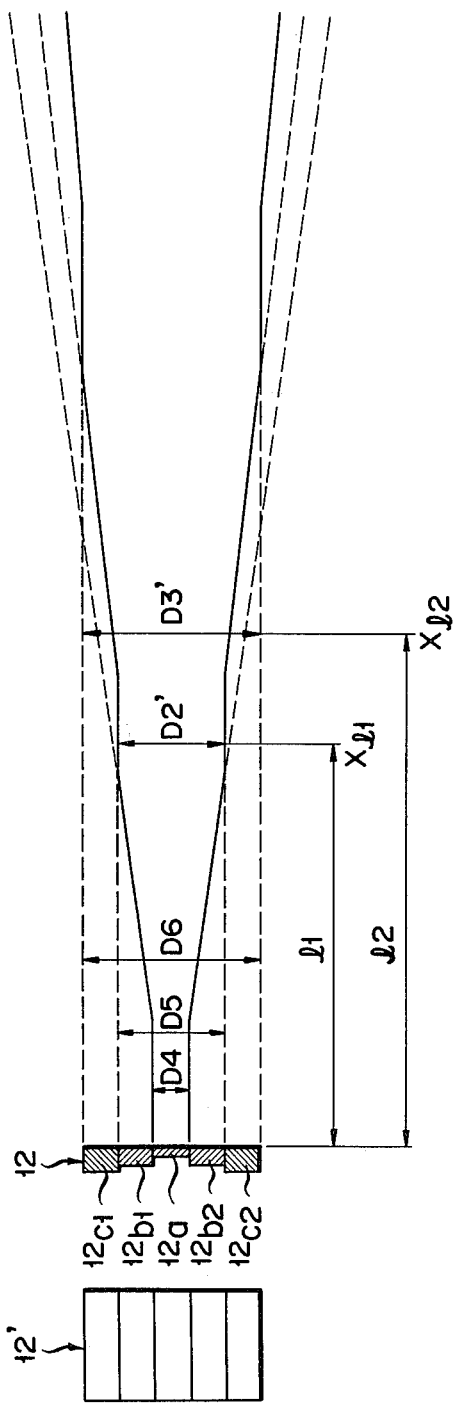
FIG. 3 shows an explanatory diagram of an ultrasound diagnosis apparatus shown in FIG. 2.
Figure 4:
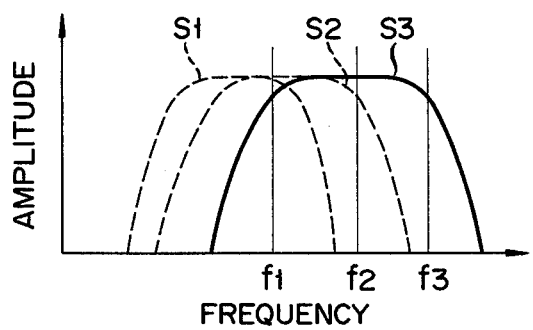
FIG. 4 shows a graph illustrating frequency distributions of ultrasounds radiated from a transducer according to the present invention.

A ultrasound field formed by the ultrasound transducer shown in FIG. 2 is as shown in FIG. 3. Incidentally, a plan view of the transducer 12 is indicated by reference numeral 12'. Frequency spectrum of the ultrasound wave radiated by the transducer elements are distributed such that as the transducer elements are thinner, the spectrum of the ultrasound waves radiated from the transducer elements have higher frequencies. This is well illustrated in FIG. 4. In the figure, a curve denoted as S1 in FIG. 3 radiated from the thickest transducer elements 12c1 and 12c2 located at the outer side of the transducer array 12 are located in the lower frequency region. A curve denoted as S2 is depicted by the ultrasound radiated from the elements 12b1 and 12b2 and is located in a higher frequency region than the curve S1. A curve S3 is for the ultrasound radiation from the thinnest element 12a and is located at the highest frequency region. These transducer elements are concurrently driven to form a resultant curve of these curves S1 to S3. In FIG. 4, f1 to f3 indicates the center frequency of the frequency bands of the filter 14 of which characteristics are illustrated in FIG. 5. Incidentally, individual positions in the ultrasound field have different spectrum, respectively. If the filter characteristic of the filter 14 is set to the curve F3 with the center frequency f3 shown in FIG. 5, the ultrasound component radiated from the transducer element 12a is received and the effective width of the transducer array 12 is D4 as shown in FIG. 3 which is the diameter of the ultrasound beam from the thinnest element 12a. If the curve F2 with the center frequency f2 is selected, the effective width of the transducer 12 is D5 which is the sum of the diameters of the beams from the transducer elements 12a and 12b1 and 12b2. Similarly, the filter 14 is set to have the characteristic curve F3 with the center frequency f3, the effective width of the transducer is D6 the sum of the widths of the beams from the transducer elements 12a, 12b1, 12b2, 12c1 and 12c2. With this combination of the transducer elements with different widths and the filter 14 with a variable frequency band, the effective width of the transducer can be adjusted by changing the center frequency of the filter 14.

In this way, for taking a tomogram of a portion of the living body in the vicinity of the transducer 12, the filter 14 is set to the center frequency f3. At this time, the portion can be tomographed with the transducer width of D4 equal to the diameter of the beam from the thinnest transducer element 12a. The resolution of the tomogram taken is defined by the diameter D4. For tomographing a portion located at a position $X_{l1}$ distanced l1 from the transducer 12, the center frequency f2 is selected for the filter 14. The diameter D5 defines the resolution of tomogram taken. Similarly, for taking a tomogram of a portion at a position $X_{l2}$ distanced l2 from the transducer 12, the center frequency f3 is selected for the filter 14. A tomogram taken has a resolution depending on the diameter D6. In this manner, the center frequency of the frequency band of the filter 14 is selected according to a depth of a desired portion to be diagnosed from the transducer 12, thereby to have the best resolution at that portion.

The band pass filter 14 in the above-mentioned embodiment may be replaced by a high pass filter of which the cut off frequency is variable.

Figures 8A, 8B, 8C, 8D:
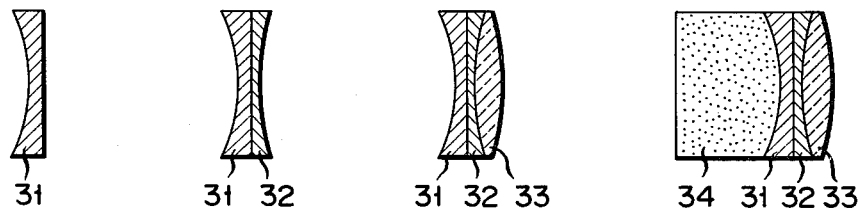
FIGS. 8A to 8D show other transducer elements than the transducer element in FIG. 2.
Figure 9:
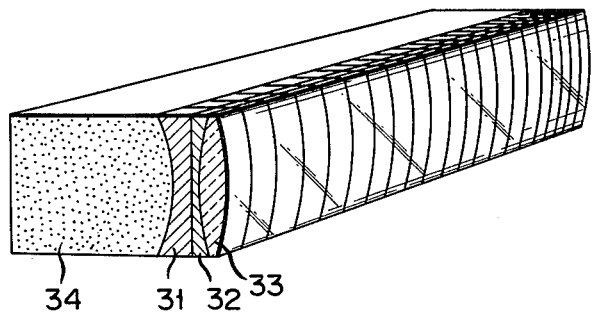
FIG. 9 shows a perspective view of a transducer using a plurality of the transducer elements shown in FIGS. 8A to 8D.

It should be understood that the present invention may variously be modified or changed within the spirit of the invention. A transducer element 31 shown in FIG. 8A has a cross section continuously and inwardly curved at one side. A number of the transducer elements 31 with such a configuration are arrayed as shown in FIG. 9 when used as a transducer. A transducer element shown in FIG. 8B is a modification of the transducer element shown in FIG. 8A, and uses additionally an impedance matching layer 32. A transducer element shown in FIG. 8C uses additionally an acoustic lens 33. A transducer element shown in FIG. 8D is further provided with an acoustic load member 34 layered on the transducer element 31. In FIG. 9, like numerals are used for designating like parts in FIGS. 8A to 8D and no further explanation is given for simplicity. When the transducer shown in FIG. 9 is used in combination with the filter 14 with a variable frequency band, the effective width of the transducer 12 can be changed and the resolution of a tomogram can be improved.

As described above, the present invention can improve a resolution of a tomogram by selecting the width of the transducer according to a depth of the portion under diagnosis of a living body.

What is claimed is:

1. An ultrasonic diagnosis apparatus comprising:
   transducer means, comprising a linear array of transducer elements sequentially disposed in a direction for directing pulses of ultrasonic energy in the form of a beam into an object and receiving echoes of said pulses to convert said echoes to electrical signals, the thickness of said transducer elements increasing from transducer elements at a central portion of said array to transducer elements toward both edges in said direction, the frequency of said ultrasonic energy radiated by each of said transducer elements being inversely related to the thickness of each of said transducer elements;
   means for energizing said transducer; and
   filter means for selectively filtering said electrical signals to pass frequency components of said electrical signals associated with selected frequencies of said ultrasonic energy and not pass other frequency components of said electrical signals, the arrangement of said elements of said transducer means and said filter means cooperating to cause the width of said ultrasonic beam at the outlet of said transducer means to vary with the selected frequency components of said electrical signals passed by said filter means.

2. An ultrasound diagnosis apparatus according to claim 1, wherein the thicknesses of said transducer elements continuously increase from the center portion toward both edges.

3. An ultrasound diagnosis apparatus according to claim 1, wherein the thickness of said transducer elements stepwise increase from the center portion toward both edges.

4. An ultrasound diagnosis apparatus according to claim 1, wherein said filter means is a band pass filter of which the center frequency is variable.

5. An ultrasound diagnosis apparatus according to claim 1, wherein said filter means is a high pass filter of which the cut-off frequency is variable.

* * * * *